US006620191B1

United States Patent
Svensson

(10) Patent No.: US 6,620,191 B1
(45) Date of Patent: *Sep. 16, 2003

(54) SYSTEM FOR RELEASABLY SECURING A STENT ON A CATHETER ASSEMBLY AND METHOD OF USE

(75) Inventor: Björn G. Svensson, Morgan Hill, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 115 days.

This patent is subject to a terminal disclaimer.

(21) Appl. No.: 09/819,222

(22) Filed: Mar. 27, 2001

(51) Int. Cl.[7] ................................................. A61F 2/06
(52) U.S. Cl. ...................................................... 623/1.11
(58) Field of Search ................................ 606/108, 198; 623/1.11, 1.12; 604/96

(56) References Cited

U.S. PATENT DOCUMENTS

| | | |
|---|---|---|
| 2,701,559 A | 2/1955 | Cooper |
| 4,323,071 A | 4/1982 | Simpson et al. |
| 4,338,942 A | 7/1982 | Fogarty |
| 4,439,185 A | 3/1984 | Lundquist |
| 4,516,972 A | 5/1985 | Samson |
| 4,538,622 A | 9/1985 | Samson et al. |
| 4,554,929 A | 11/1985 | Samson et al. |
| 4,573,470 A | 3/1986 | Samson et al. |
| 4,608,984 A | 9/1986 | Fogarty |
| 4,616,652 A | 10/1986 | Simpson |
| 4,638,805 A | 1/1987 | Powell |
| 4,702,252 A | 10/1987 | Brooks et al. |
| 4,733,665 A | 3/1988 | Palmaz |
| 4,748,982 A | 6/1988 | Horzewski et al. |
| 4,880,683 A | 11/1989 | Stow |
| 4,950,227 A | 8/1990 | Savin et al. |
| 4,994,033 A | 2/1991 | Shockey et al. |
| 5,037,392 A | 8/1991 | Hillstead |
| 5,059,169 A | 10/1991 | Zilber |

(List continued on next page.)

FOREIGN PATENT DOCUMENTS

| | | | |
|---|---|---|---|
| EP | 0 553 960 A1 | | 8/1993 |
| EP | 0 834 293 A1 | | 4/1998 |
| EP | 0 974 315 A1 | | 1/2000 |
| SU | 1477423 | | 5/1989 |
| WO | WO 95/33422 | * | 12/1995 |
| WO | WO 98/07390 | | 2/1998 |

OTHER PUBLICATIONS

ACS RX Multi–Link™ Coronary Stent System Brochure (Undated), 7 pages.

Primary Examiner—David J Isabella
Assistant Examiner—Kamrin Landrem
(74) Attorney, Agent, or Firm—Fulwider Patton Lee & Utecht, LLP

(57) ABSTRACT

The invention is directed to an improvement in stent delivery systems and method for releasably securing a stent onto an expandable member of a catheter. A deformable material is applied between the outer surface of the expandable member and the stent mounted thereon. The deformable material is affixed to an expandable member, similar to a dilatation balloon and is sufficiently compliant to be deformed by compressive engagement with the stent. The deformable material beneath the stent is compressed, projecting a portion of the material adjacent struts of the stent into a physical stop that impedes lateral movement of the stent relative to the balloon during delivery to the target site. The deformable material may be an adhesive or a curable compound in a cured or uncured state. The deformable material may be brought into releasably secure contact with the stent by shifting the stent toward the balloon, the balloon toward the stent, or both. Shifting the stent toward the balloon may include crimping the stent.

30 Claims, 3 Drawing Sheets

U.S. PATENT DOCUMENTS

| | | |
|---|---|---|
| 5,064,435 A | 11/1991 | Porter |
| 5,078,720 A | 1/1992 | Burton et al. |
| 5,100,429 A | 3/1992 | Sinofsky et al. |
| 5,108,416 A | 4/1992 | Ryan et al. |
| 5,116,318 A | 5/1992 | Hillstead |
| 5,156,911 A | 10/1992 | Stewart |
| 5,158,548 A | 10/1992 | Lau et al. |
| 5,226,889 A | 7/1993 | Sheiban |
| 5,242,399 A | 9/1993 | Lau et al. |
| 5,344,426 A | 9/1994 | Lau et al. |
| 5,360,401 A | 11/1994 | Turnland |
| 5,387,450 A | 2/1995 | Stewart |
| 5,409,495 A | 4/1995 | Osborn |
| 5,412,035 A | 5/1995 | Schmitt et al. |
| 5,445,646 A | 8/1995 | Euteneuer et al. |
| 5,451,233 A | 9/1995 | Yock |
| 5,458,615 A | 10/1995 | Klemm et al. |
| 5,476,476 A | 12/1995 | Hillstead |
| 5,496,346 A | 3/1996 | Horzewski et al. |
| 5,501,227 A | 3/1996 | Yock |
| 5,507,768 A | 4/1996 | Lau et al. |
| 5,514,154 A | 5/1996 | Lau et al. |
| 5,571,135 A | 11/1996 | Fraser et al. |
| 5,645,559 A | 7/1997 | Hachtman et al. |
| 5,653,691 A | 8/1997 | Rupp et al. |
| 5,667,523 A | 9/1997 | Bynon et al. |
| 5,695,498 A | 12/1997 | Tower |
| 5,700,286 A | 12/1997 | Tartaglia et al. |
| 5,720,726 A | 2/1998 | Marcadis et al. |
| 5,746,745 A | 5/1998 | Abele et al. |
| 5,759,474 A | 6/1998 | Rupp et al. |
| 5,810,871 A | 9/1998 | Tuckey et al. |
| 5,830,217 A | 11/1998 | Ryan |
| 5,836,965 A | 11/1998 | Jendersee et al. |
| 5,893,852 A | 4/1999 | Morales |
| 5,976,155 A * | 11/1999 | Foreman et al. ............ 623/1.11 |
| 6,027,510 A | 2/2000 | Alt |
| 6,051,021 A | 4/2000 | Frid |
| 6,059,810 A | 5/2000 | Brown et al. |
| 6,063,092 A | 5/2000 | Shin |
| 6,066,156 A | 5/2000 | Yan |
| 6,086,610 A | 7/2000 | Duerig et al. |
| 6,099,559 A | 8/2000 | Nolting |
| 6,106,530 A | 8/2000 | Harada |
| 6,110,180 A | 8/2000 | Foreman et al. |
| 6,123,712 A | 9/2000 | Di Caprio et al. |
| 6,159,227 A | 12/2000 | Di Caprio et al. |
| 6,168,617 B1 | 1/2001 | Blaeser et al. |
| 6,174,316 B1 | 1/2001 | Tuckey et al. |
| 6,193,727 B1 * | 2/2001 | Foreman et al. ............ 606/108 |
| 6,217,586 B1 | 4/2001 | Mackenzie |
| 6,245,076 B1 | 6/2001 | Yan |
| 6,258,099 B1 | 7/2001 | Mareiro et al. |
| 6,277,110 B1 | 8/2001 | Morales |
| 2001/0016753 A1 | 8/2001 | Caprio et al. |

* cited by examiner

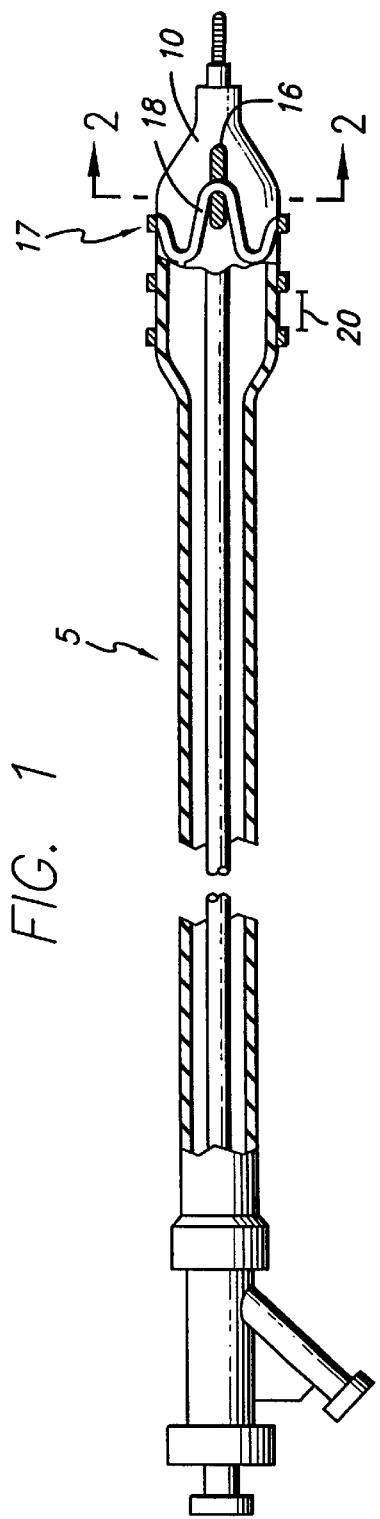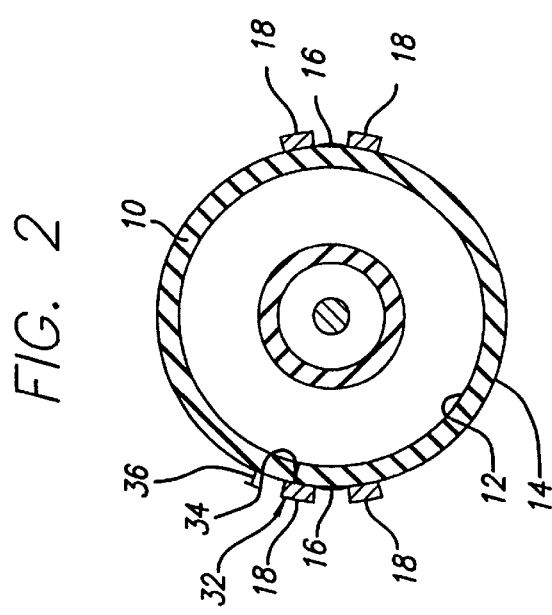

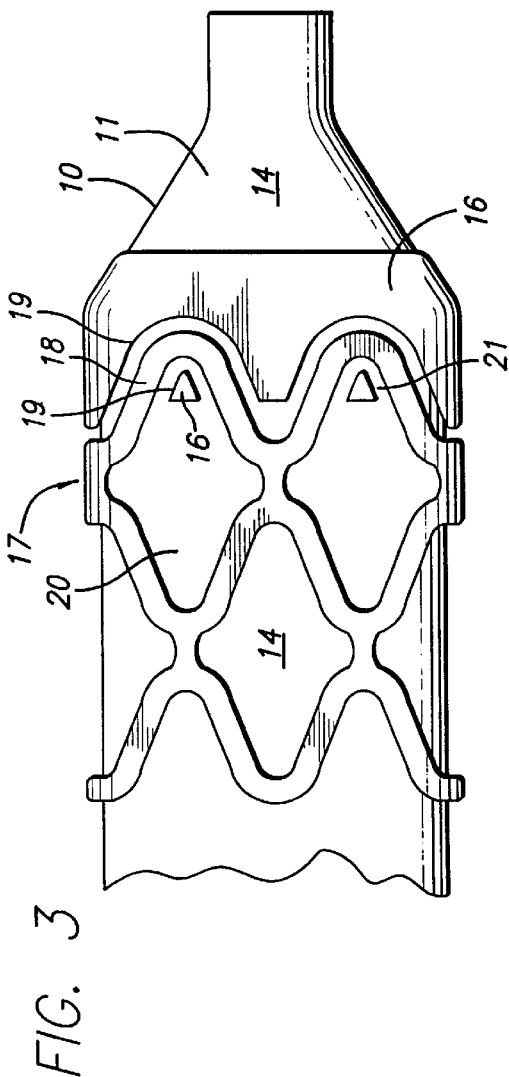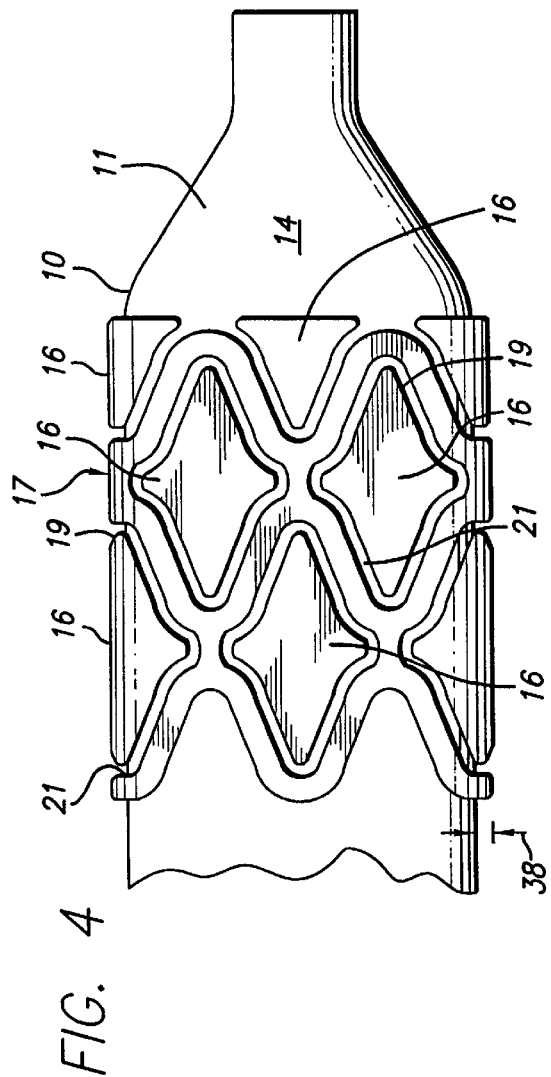

SYSTEM FOR RELEASABLY SECURING A STENT ON A CATHETER ASSEMBLY AND METHOD OF USE

BACKGROUND OF THE INVENTION

This invention relates to devices for the treatment of heart disease and particularly to endo-arterial prostheses, which are commonly called stents. More particularly, the invention relates to catheter assemblies for releasably securing the stent to the catheter during delivery through a body lumen.

Several interventional treatment modalities are presently used for heart disease including balloon and laser angioplasty, atherectomy and by-pass surgery. In typical balloon angioplasty procedures, a guiding catheter having a performed distal tip is percutaneously introduced through the femoral artery into the cardiovascular system of a patient in a conventional Seldinger technique and advanced within the cardiovascular system until the distal tip of the guiding catheter is seated in the ostium.

A guide wire is positioned within an inner lumen of a dilatation catheter and then both are advanced through the guiding catheter to the distal end thereof. The guide wire is first advanced out of the distal end of the guiding catheter into the patient's coronary vasculature until the distal end of the guide wire crosses a lesion to be dilated, then the dilatation catheter having an inflatable balloon on the distal portion thereof is advanced into the patient's coronary anatomy over the previously introduced guide wire until the balloon of the dilatation catheter is properly positioned across the lesion.

Once in position across the lesion, the balloon, which is made of relatively inelastic materials, is inflated to a predetermined size with radiopaque liquid at relatively high pressure (e.g., greater than 4 atmospheres) to press the arteriosclerotic plaque of the lesion against the inside of the artery wall and to otherwise expand the inner lumen of the artery. The balloon is then deflated so that blood flow can be resumed through the dilated artery and the dilatation catheter can be removed therefrom.

Further details of dilatation catheters, guide wires, and devices associated therewith for angioplasty procedures can be found in U.S. Pat. No. 4,323,071 (Simpson-Robert); U.S. Pat. No. 4,439,185 (Lindquist); U.S. Pat. No. 4,516,972 (Samson), U.S. Pat. No. 4,538,622 (Samson, et al.); U.S. Pat. No. 4,554,929 (Samson, et al.); U.S. Pat. No. 4,616,652 (Simpson); U.S. Pat. No. 4,638,805 (Powell); U.S. Pat. No. 4,748,982 (Horzewski, et al.); U.S. Pat. No. 5,507,768 (Lau, et al.); U.S. Pat. No. 5,451,233 (Yock); and U.S. Pat. No. 5,458,651 (Klemm, et al.), which are hereby incorporated herein in their entirety by reference thereto.

One problem which can occur during balloon angioplasty procedures is the formation of intimal flaps which can collapse and occlude the artery when the balloon is deflated at the end of the angioplasty procedure. Another problem characteristic of balloon angioplasty procedures is the large number of patients which are subject to restenosis in the treated artery. In the case of restenosis, the treated artery may again be subjected to balloon angioplasty or to other treatments such as by-pass surgery, if additional balloon angioplasty procedures are not warranted. However, in the event of a partial or total occlusion of a coronary artery after the balloon is deflated, the patient may require immediate medical attention, particularly in the coronary arteries.

A focus of recent development work in the treatment of heart disease has been directed to endoprosthetic devices called stents. Stents are generally cylindrically shaped intravascular devices which are placed within an artery to hold it open. The device can be used to prevent restenosis and to maintain the patency of a blood vessel immediately after intravascular treatments. In some circumstances, they can also be used as the primary treatment device where they are expanded to dilate a stenosis and then left in place.

One method and system developed for delivering stents to desired locations within the patient's body lumen involves crimping a stent about an expandable member, such as a balloon on the distal end of a catheter, advancing the catheter through the patient's vascular system until the stent is in the desired location within a blood vessel, and then inflating the expandable member on the catheter to expand the stent within the blood vessel. The expandable member is then deflated and the catheter withdrawn, leaving the expanded stent implanted within the blood vessel, holding open the passageway thereof.

However, retaining the position of the stent in the proper location on the expandable member while advancing the catheter through the body lumen has been found to be difficult. If the stent is dislodged from or moved on the expandable member the system will not correctly deliver the stent into the body lumen. This would require repeating the procedure. This delays insertion of the stent into the body lumen which may adversely affect the patient's health.

Different methods have been attempted to maintain the position of the stent on the expandable member. One such method involves a protective sheath surrounding the catheter and stent assembly, which is retracted prior to inflation of the expandable member. The use of the sheath, however, increases the profile of the catheter assembly which must traverse narrow vessels. It would be an improvement to use a technique which does not increase the overall profile of the catheter assembly.

Another method has been to remove the friction reducing coating on the expandable member in the location of the stent thereby allowing the catheter assembly's pre-coated surface to hold the stent in frictional contact. This method has not proven highly efficient in maintaining the stent in the desired location.

Still another method involves application of high pressure to force the inflation balloon into gripping contact with gaps or openings between struts in the stent wall. Should the gaps between stent struts be relatively small, however, such a method may have limitations. Other methods require heat to flow balloon material into the gaps or a balloon coating.

What has been needed is a reliable and convenient means of maintaining a stent in a desired location on a stent delivery system without substantially increasing the overall profile of the catheter assembly. The present invention satisfies this need.

SUMMARY OF THE INVENTION

This invention is directed to an improvement in stent delivery systems for releasably securing a stent onto an expandable member of a catheter. The improvement of this invention includes placing deformable material between the outer surface of the expandable member and the stent coaxally disposed thereon. The deformable material is affixed to an expandable member, such as a dilatation balloon and is sufficiently compliant to be deformed by compressive engagement with the stent. The material sandwiched between the expandable member and the stent is compressed projecting a portion of the material adjacent the stent into a physical stop that impedes lateral movement of the stent relative to the balloon during travel to the target site. The deformable material may be an adhesive or a curable compound in a cured or uncured state. The affixed material may be brought into releasably secure contact with the stent by closing the stent inwardly toward, and into engagement with, the underlying expandable member, expanding the expandable member outwardly toward, and into engagement with, the stent, or both. Compressing the stent toward the balloon may include crimping the stent. Once at the target site, the stent is expanded by way of inflation of the expandable member. Any adhesive contact between the stent and the expandable member is broken and the stent is expanded to its implanted diameter. The expandable member is deflated and withdrawn from the patent leaving the stent implanted in a body lumen, such as a coronary artery.

The deformable material is applied to the outer surface of the balloon followed by the coaxial mounting of the stent thereover. In the adhesive form, the deformable material can be applied in a thin layer over selected portions of the balloon surface to provide, upon crimping of the stent, inflation of the balloon, or both, adhesive engagement with the stent. Deformable material may be applied, whether adhesive or otherwise, to the balloon so that as the material becomes compressed it forms physical stops adjacent to stent struts, the stops serving to block longitudinal movement of the stent relative to the expandable member. Deformable material may also be applied in sufficient thickness, up to the thickness of the stent wall, to form a continuous smooth outer surface of the distal portion of the assembly without substantially increasing the insertion profile of the stent.

Affixed to the outer surface of a dilatation balloon, the unexpanded stent is transported as part of the catheter assembly through the vessel pathway to the desired stenotic site. Once at the site, the balloon is inflated transferring circumferential expansion force to the expandable stent. Subjected to such force from the balloon, the stent is expanded against the vessel wall to the desired configuration. The balloon is then deflated, unsecured from the expanded stent, and withdrawn leaving the expanded stent to support the vessel wall.

Should the stent become adhered to the material, the expansion and contraction forces imparted by the balloon to the material serve to dislodge the material from the stent. If the deformable material is an adhesive and is at least substantially tacky at the time of contact with the stent, it is preferable that the deformable material have greater affinity for the balloon than to the stent so that the material remains affixed to the balloon upon deflation and withdrawal of the balloon.

Preference for adherence of the material to the balloon is provided in a number of ways. For example, the composition of the outer surface of the balloon and the inner surface of the stent may differ so that the material adheres more strongly to the expandable member. Silastic rubber and Nylon, for example, are often used as balloon material. Adhesion to such materials are typically greater than, for example, stainless steel, a widely used stent material. Additionally, adhesive may be formulated to covalently bond to the balloon material which is often made from polyethylene (PE), polyethylene terephthalate (PET), or Nylon.

If adherence properties of the stent and balloon surfaces are not substantially different, a curable adhesive, for example, may be utilized so that affixation to the balloon occurs when adhering properties of the adhesive are greater when applied to the balloon than when later compressively or adhesively engaged to the stent. After curing, the adhering properties of the adhesive are decreased, so that the stent may be crimped over the material resulting in a weaker interface between the stent surface and the adhesive than to the balloon surface and the adhesive. The adhesive should be applied so that it separates from the stent no later than at maximum deflation of the expandable member at the implant site.

The degree of tackiness or stickiness of the adhesive of the present invention may be chosen from a variety of deformable materials such as polymers, urethanes, and adhesives of varying adhesive strengths as desired. Adhesive may be chosen in consideration of a number of factors including, but not limited to, the rigors and forces expected to be encountered by the stent and the expandable member during travel to the stenotic site, the extent of frictional resistance provided by the mounting and crimping of the stent onto the expandable member, and the extent of separation force made available by the inflation and deflation of the expandable member. After the deformable adhesive is applied, the stent is positioned over the adhesive and is tightly crimped, and/or the balloon is expanded, into compressing and/or adhesive engagement with the adhesive.

The balloon is preferably folded prior to application of the material in typical S or tripartate propeller fashion exposing balloon wing edges. In one embodiment, the deformable material is applied to the wing edges. Application of the material to the interior of the balloon folds is preferably avoided so that the folded wings of the balloon do not stick together thereby inhibiting expansion and so that the material does not cause unnecessary buildup of the insertion profile of the assembly.

The deformable material, whether in the form of an adhesive or otherwise, may be applied sparingly so that the folded profile of the balloon is not increased substantially and so that the stent is easily separated from the balloon when the balloon is inflated and deflated. Sparse application may be as small as a dot or drop of deformable material not exceeding a thickness of 0.01 centimeter, for example, or may be, in another example, a bead of deformable material placed longitudinally along or circumferentially radially about the outer surface of the balloon. The thickness of the dot or drop or bead of deformable material can range from about 0.001 to 0.01 cm, but may be larger or smaller depending upon the application.

The material may be cured or uncured prior to engagement with the stent. By way of example, nine drops of UV curable Dymax polyurethane can be applied sparingly to a tripartite balloon, three drops along each of the three folded wing edges at the proximal, middle, and distal sections of the balloon. The polyurethane can be fully cured prior to crimping to provide a very soft, flexible, and somewhat sticky or tacky surface. The stent thereafter can be positioned coaxially over the cured material and crimped tightly to compress the material to form one or more physical stops adjacent one or more stent struts.

Compression of at least some of the material beneath the stent struts may serve to force the deformable material into one or more gaps adjacent the struts and/or adjacent one or more end struts. The material formed adjacent the struts forms physical stops blocking movement of the stent relative to the balloon during travel to the stenotic site. If the material is sufficiently thick it may also contact the wall surfaces of the stent struts defining the depth of the gaps and may thereby provide, upon cure, additional adhesion and/or frictional contact with the stent before stent expansion.

The depth of the deformable material, whether in the gaps, beneath the stent struts, or otherwise, may be controlled. A smooth outer stent surface may be achieved by compressing the struts in sufficient deformable material. However, so that the insertion profile of the catheter assembly is not substantially increased, the deformable material should not exceed the thickness of the stent. The thickness of the stent can vary widely as is known in the art. Typical stent thicknesses range from about 0.0015 to about 0.050 inch (0.0381 to 1.27 mm), but can vary considerably from these dimensions depending upon a particular application, such as use in coronary or peripheral vessels. Additionally, care must be taken not to submerge the stent struts into the material to such an extent that expansion of the stent and detachment of the stent from the expandable member is prevented. Manufacture of the assembly may be under standard atmospheric pressure, humidity, and at room temperature. Application of extraneous heat is unecessary.

After travel to the stenotic site in the unexpanded state, the radial circumference of the balloon is increased by inflation. With expansion of the outer surface of the balloon, the stops formed adjacent the stent struts move outwardly and away from one another and away from the struts of the expanding stent to form proximal gaps between the struts and the stops. The movement of the stops away from the struts increases the freedom of movement of the struts and enhances disengagement of the expandable member from the stent upon deflation.

In lieu of, or in addition to crimping, the deformable material affixed to the balloon may be shifted into compressing engagement with the stent by way of inflation of the balloon toward the stent. During manufacture, a containing device, such as a sheath, should be placed over the stent to prevent premature expansion and to maintain the stent in a low insertion profile. However, the stent may be unconstrained if the deformable material is sufficiently pliable to be compressed by the stent without causing expansion of the stent. Uncured polyurethane or polymeric foam, for example, is such a sufficiently pliable material.

The invention can be used with the known configurations of stent delivery systems including, for example, over-the-wire (OTW) intravascular catheters, monorail catheters, and rapid exchange (Rx) intravascular catheters.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 1 is a partial cross-sectional view depicting the stent delivery system incorporating the invention.

FIG. 2 is a transverse cross-sectional view taken along lines 2—2 in FIG. 1.

FIG. 3 is an enlarged plan view of an expanded expandable member and an expanded expandable stent depicting the stent compressed in the deformable material of the invention.

FIG. 4 is an enlarged plan view of an expanded expandable member and an expanded stent depicting the stent compressed in the deformable material of the invention.

DETAILED DESCRIPTION OF PREFERRED EMBODIMENTS

Figure 5:
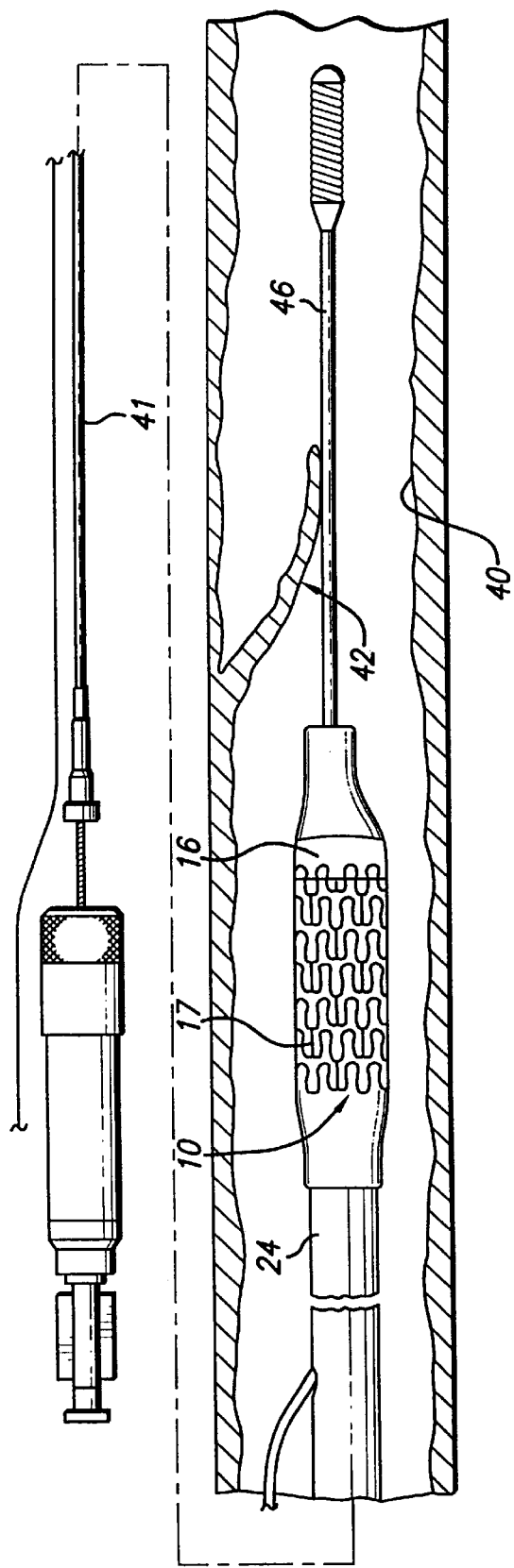
FIG. 5 is a longitudinal plan view of a rapid exchange (Rx) catheter depicting stent struts and deformable material of the invention and inserted into a body lumen.

Stent delivery systems are typically composed of a catheter assembly having an expandable member such as an inflatable dilatation balloon located at a distal section of the assembly. Stents are typically in the shape of a tubular wall of a lattice configuration formed by struts with gaps therebetween.

The present invention results in a simplified method of retaining the stent on the catheter while inserting the stent into the body lumen. The catheter assembly of the invention is inserted into the body lumen without further steps being taken to prevent the dislocation of the stent. The expandable member is inflated at the desired location expanding the stent into contact with the lumen. As the expandable member is inflated and then deflated, the stent is released from the deformable material and the remainder of the catheter assembly[]may be withdrawn leaving the stent implanted within the body lumen.

FIGS. 1 and 2 illustrate catheter assembly 5 which releasably secures a stent and embodies the features of the invention. Generally, the catheter assembly includes an expandable member 10 having an inner surface 12 and an outer surface 14 and having curable deformable material 16 extending outwardly from the outer surface. An expandable stent 17 is positioned coaxially about the expandable member. The stent is shaped as a tubular wall having a lattice configuration defined by struts 18 and gaps 20 therebetween.

The deformable material 16 of the present embodiment is a curable adhesive and is applied in a thin longitudinal bead to the outer surface 14 of the expandable member 10. The adhesive is cured prior to contact with the stent and maintains a pliable, compressible surface. The expandable stent 17 is crimped about expandable member 10 and into releasably adhesive engagement with at least a portion of deformable material. This configuration removeably secures the stent to the expandable member and impedes movement between the stent and the expandable member during travel to the stenotic site.

The deformable material 16 may be applied in an amount as small as a dot of material no greater than about 1.0 mm thick on outer surface 14 of expandable member 10. Application of the material may be accomplished by using a pointed mandrel tool loaded with a minute drop of the deformable adhesive and dottingly applying the adhesive onto the expandable member, or by applying the dots with a machine designed for precise placement if the stent is to be precisely aligned over the material. Physical stops, for example, may be formed by increasing crimping force, applying a thickened amount of material to the balloon, or compressing the uncured material.

The deformable material may selected from a variety of polymers such as polyurethane, polyethylene (PE), or polyethylene teraphthalate (PET), and may be curable and may contain adhesive. Examples of a curable material are UV-curable Dymax Polyurethane and UV-curable anaerobic polymer commercially available under the tradename LOCTITE 33-11 from the Loctite Corp. Depending on the material used, different curing methods are available. These methods include application of heat or time and are known to those in the art.

The invention can be configured with known stent delivery systems. On many of these catheter systems, expandable member 10 is similar to an inflatable dilatation balloon. FIGS. 1 and 2 show catheter assembly 5 as including an over-the-wire (OTW) intravascular catheter, which is known in the art.

FIG. 3 illustrates another configuration for the deformable material 16. In this configuration, the stent 17 and the expandable member 10 are in an expanded state, the stent being releasably compressed in the deformable material. The current embodiment is formed with deformable material applied uncured in a continuous circumferential radial band to the outer surface 14 of the distal end 11 of an unfolded expandable member. The stent is thereafter crimped onto the expandable member and compressed in the deformable material. The material is then cured prior to traveling to the stenotic site. The stent is thereafter expanded by inflation of the expandable member implanting the stent followed by reduction and withdrawal of the expandable member.

When compressed, the material is of sufficient thickness to provide physical stops 19 to block movement of the stent 17 relative to the expandable member 10 during travel to the target or stenotic site. Stops may also be formed by projection of compressed material from beneath the stent or may be formed by compression of the inner surface of the stent below the outer surface of the material. Providing stops at the distal end of the stent inhibits slippage, peeling back, and longitudinal compression of the stent during forward travel to the stenotic site. Such distal placement also provides for a smoothed transition for the vessel to receive and accept the profile of the advancing stent. Such a smoothed transition also provides for treatment of more distal anatomy.

Material may also be applied beneath the proximal end of the stent. Stops formed thereby inhibit stretching of the stent during advancement through a vessel. If catheter withdrawal is necessary, the stops 19 inhibit longitudinal compression and peeling back of the stent. Stops may also be formed beyond the ends of the stent to help secure the stent during advancement or withdrawal through a vessel.

Once at the target or stenotic site, the expandable member is expanded to expose proximal gaps 21 between the cured material 16 and the stent struts 18. The proximal gaps facilitate expansive movement of the stent struts 18 during expansion of the stent. The proximal gaps also facilitate release of the material from the stent upon deflation of the expandable member so that the stent may be unsecured from the expandable member.

In other embodiments, in lieu of or in addition to crimping, the stent may be compressed in the deformable material by expanding the expandable member, with deformable material affixed thereon, into compressing or adhesive engagement with the inner surface of the stent. The stent may be compressed toward the expandable member by crimping the stent, the expandable member may be expanded toward the stent by expansion of the expandable member, or the member and stent may be shifted toward one another by a combination of crimping and expansion.

Use of easily compressible deformable material such as uncurred polyurethene or polymeric foam may be especially beneficial when gaps between struts are relatively narrow. Easily compressible material also eliminates the need for a containment sheath when mounting the stent on the balloon as the force required to compress the material during manufacture may be less than that required to expand the stent.

FIG. 4 illustrates another embodiment for the configuration of the stent 17 and the deformable material 16. In this configuration, the material is applied uncured to the outer surface 14 of the expandable member 10. The stent is thereafter releasably compressed into the material and cured. Thickness 38 of the material is substantially equal to the thickness 36 of the expandable stent 17, so that the surface of the assembly is relatively smooth in the location of the stent and the material. In this configuration, not only does the invention greatly impede relative motion of the stent by formation of stops 19 adjacent each of the struts, the smoothed surface also decreases the risk that a portion of the stent will snag in a tortuous vessel such as on a calcified lesion.

In another embodiment of the invention, the stent is releasably compressed into cured deformable material so that the material beneath the stent struts is compressed. The uncompressed material in the gaps forms stops impeding movement of the stent relative the expandable member during unexpanded travel to the stenotic site.

Figure 7:
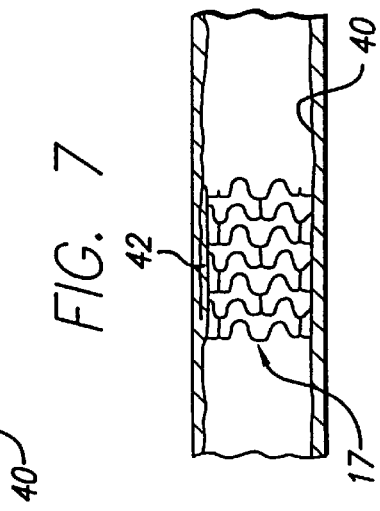
FIG. 7 is a longitudinal plan view depicting the stent implanted in the body lumen and the stent delivery system removed.
Figure 6:
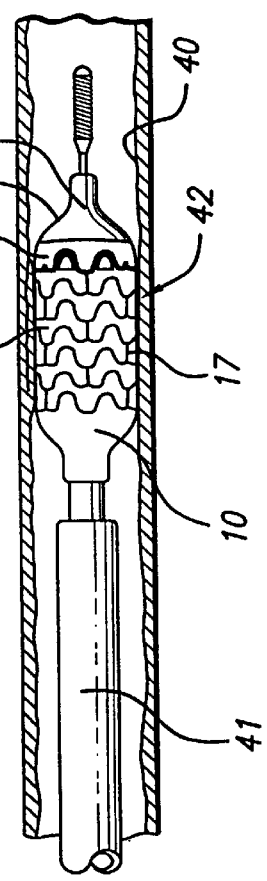
FIG. 6 is a longitudinal plan view of a stent delivery system having stent struts compressed in deformable material and depicting the expandable member being inflated and the stent implanted.

In another method of use, the catheter assembly having a releasably secured expandable stent 17 is used for delivering and implanting the stent into a body lumen when used in combination with a stent delivery system. These systems include over-the-wire (OTW) catheters (FIG. 1) and rapid exchange (Rx) catheters (FIGS. 5–7). FIGS. 5–7 illustrate an exemplary use of the invention using an Rx catheter. The catheter assembly with expandable stent 17 held firmly in place on expandable member 10 is inserted into body lumen 40 using stent delivery system 41. The figures illustrate one situation in which the invention is used after an intravascular procedure has caused dissection 42 in the arterial lining to such an extent that the lining needs support to prevent it from collapsing into the arterial passage way and obstructing flow through the vessel. In these situations, as others, the invention allows the stent to be delivered to target location 42 without further means to retain the stent on the expandable member.

Preferably, stent delivery system 41 is advanced over guide wire 46 which is already in position distal to target location 42. Since the stent 17 is releasably attached to the expandable member 10 during delivery through the patient's vasculature, it will not move relative to the expandable member until it is positioned at the target location. The deformable material 16 retains the stent until expansion is desired and the stent is implanted. As illustrated in FIG. 6, expandable member 10 is inflated thereby expanding and implanting expandable stent 17 into body lumen 40. This may be accomplished, for example, by introducing radiopaque fluid into the interior of the expandable member under substantial pressure as is known in the art. The expandable member is then deflated and the expandable stent remains expanded and in place in the target location of the body lumen. With the expandable stent in the expanded condition, and the expandable member in the deflated condition, the deformable material, being affixed to the outer surface 14 of the expandable member, no longer extends into gaps 20 of the expandable stent. In the event the deformable material is an adhesive, adhesion to the expandable member is preferred, facilitating release of the adhesive from the stent upon expansion and contraction of the expandable member. While the expandable stent remains implanted in the target location of the body lumen, the catheter assembly is withdrawn from the body lumen.

The dimensions of the intravascular catheter will generally follow the dimensions of intravascular catheters used in angioplasty procedures in the same arterial location.

Typically, the length of a catheter for use in the coronary arteries is about 150 cm, the outer diameter of the catheter shaft is about 0.035 inch (0.89 mm), the length of the balloon is typically about 20 mm and the inflated diameter about 1 to about 8 mm. These dimensions can vary widely and, for example, the diameters would be substantially bigger for peripheral applications.

The materials of construction of the catheter and expandable member may be selected from those used in conventional stent delivery catheters.

While the present invention has been described herein in terms of delivering an expandable stent to a desired location within a patient's body lumen, the delivery system can also be employed to deliver stents to locations within other body lumens so that the stents can be expanded to maintain the patency of those body lumens. Various changes and improvements may also be made to the invention without departing from the scope thereof.

What is claimed:

1. A catheter assembly for releasably securing a stent during delivery and implanting within a body lumen, comprising:
    an elongated catheter having an expandable member disposed at a distal section of the catheter, the expandable member including a peripheral wall defining an inner surface and an outer surface;
    a layer of deformable material affixed to at least a portion of the outer surface; and
    the stent positioned about the expandable member and crimped into releasably compressing engagement with the layer of deformable material to cause a segment of the layer to form at least one physical stop to restrict movement of the stent relative to the expandable member during delivery of the stent in an unexpanded state to the desired location in the body lumen.

2. The catheter assembly of claim 1, wherein the layer of deformable material is curable.

3. The catheter assembly of claim 1, wherein the stent is formed by a wall of a lattice configuration defining stent struts with gaps therebetween and wherein at least a portion of at least one of the struts is compressed into the layer of deformable material.

4. The catheter assembly of claim 3, wherein the at least one stop is formed by projection of the compressed deformable material from beneath the compressed stent strut.

5. The catheter assembly of claim 4, wherein at least a portion of a layer of uncompressed deformable material is forced into at least one of the gaps.

6. The catheter assembly of claim 4, wherein the struts are compressed sufficiently in the layer of deformable material to form a smoothed outer surface of the distal end of the assembly.

7. The catheter assembly of claim 1, wherein the expandable member includes an inflatable balloon constructed with at least one fold, the fold having a peripheral edge, and the layer of deformable material is applied on the edge.

8. The catheter assembly of claim 7, wherein the edge includes a longitudinal proximal, mid, and distal portion and wherein the deformable material is applied in a linear pattern of at least three dots, at least one of the dots is affixed to the proximal, middle, and distal portions respectively of the edge.

9. The catheter assembly of claim 1, wherein the layer of deformable material includes polymeric foam.

10. The catheter of claim 1, wherein the layer of deformable material has a thickness no greater than about 1.0 mm.

11. The catheter assembly of claim 1, wherein the layer of deformable material covers less than the entire outer surface.

12. The catheter assembly of claim 1, wherein the layer of deformable material is a polymer.

13. The catheter assembly of claim 1, wherein the layer of deformable material is UV-curable polyurethane.

14. The catheter assembly of claim 1, wherein the layer of deformable material is soft, flexible and exhibits a sticky outer surface.

15. The catheter assembly of claim 1, wherein the layer of deformable material is configured as a longitudinal bead affixed to the surface of the expandable member.

16. The catheter assembly of claim 1, wherein the layer of deformable material is an adhesive.

17. The catheter assembly of claim 1, wherein an adhesive bond formed between the stent and the deformable material is broken when the expandable member is inflated and then deflated.

18. A method of releasably securing a stent mounted on a catheter assembly, comprising:
    providing an expandable member disposed at a distal section of a catheter, the expandable member including a peripheral wall defining an inner surface and an outer surface and a deformable material affixed to the outer surface of the peripheral wall;
    providing the expandable stent;
    positioning the stent about the expandable member; and
    crimping the stent into compressing engagement with a portion of the material to form at least one stop to restrict movement of the stent relative to the expandable member during delivery of the stent in an unexpanded state to a desired location in a body lumen.

19. The method of claim 18, wherein the deformable material is curable.

20. The method of claim 19, wherein the material is cured before crimping the stent.

21. The method of claim 19, wherein the material is cured after crimping the stent.

22. The method of claim 18, wherein the stent is formed with a tubular wall having a lattice configuration defining struts with gaps therebetween and wherein crimping the stent includes crimping at least one of the struts into compressing engagement with a portion of the material.

23. The method of claim 22, wherein the deformable material is compressed to project material in at least one of the gaps to form the at least one stop.

24. The method of claim 22, wherein the deformable material is compressed to form at least one stop adjacent to at least one of the struts.

25. The method of claim 18, wherein the deformable material is an adhesive.

26. The method of claim 25, wherein an adhesive bond is formed between the deformable material and the stent and the bond is broken when the expandable member is inflated and then deflated.

27. A method of delivering and implanting an expandable stent at a desired location in a body lumen, comprising:
    providing a catheter assembly having an expandable member defining an inner surface and an outer surface and having a deformable material affixed to the outer surface;
    providing a stent;
    positioning the stent coaxially about the expandable member;
    crimping the stent onto the expandable member and into compressing engagement with the deformable material to form at least one stop to block longitudinal movement of the stent relative to the expandable member during intraluminal delivery to the desired location in the body lumen;

advancing the catheter assembly through the body lumen to the desired location with the stent secured thereon;

inflating the expandable member to expand and implant the stent at the desired location;

deflating the expandable member to break the engagement between the stent and the deformable material; and withdrawing the catheter assembly from the body lumen.

28. The method of claim 27, wherein the deformable material is an adhesive.

29. The method of claim 27, wherein the stent is of the type formed in a tubular lattice configuration with a wall defined by stent struts with gaps therebetween and wherein at least a portion of the at least one of the struts is compressed into the deformable material to form at least one stop.

30. The method of claim 27, wherein the deformable material is curable.

* * * * *